(12) United States Patent
Mirizzi et al.

(10) Patent No.: US 7,402,320 B2
(45) Date of Patent: Jul. 22, 2008

(54) APPARATUS, MATERIAL COMPOSITIONS, AND METHODS FOR PERMANENT OCCLUSION OF A HOLLOW ANATOMICAL STRUCTURE

(75) Inventors: Michael Stephan Mirizzi, San Jose, CA (US); Halil Ibrahim Karabey, San Jose, CA (US); Anna Grace Prestezog, Sunnyvale, CA (US); Bob McRae, San Jose, CA (US)

(73) Assignee: VNUS Medical Technologies, Inc., San Jose, CA (US)

( * ) Notice: Subject to any disclaimer, the term of this patent is extended or adjusted under 35 U.S.C. 154(b) by 434 days.

(21) Appl. No.: 11/213,202

(22) Filed: Aug. 26, 2005

(65) Prior Publication Data

US 2006/0052823 A1    Mar. 9, 2006

Related U.S. Application Data

(60) Provisional application No. 60/605,843, filed on Aug. 31, 2004.

(51) Int. Cl.
*A61F 13/00* (2006.01)
(52) U.S. Cl. .................................................. 424/422
(58) Field of Classification Search .......... 424/422, 424/423; 128/831; 606/157, 158, 214
See application file for complete search history.

(56) References Cited

U.S. PATENT DOCUMENTS

| | | | |
|---|---|---|---|
| 3,739,773 A * | 6/1973 | Schmitt et al. ............... 606/62 |
| 4,002,173 A | 1/1977 | Manning et al. | |
| 4,173,228 A | 11/1979 | Van Steenwyk et al. | |
| 4,268,495 A | 5/1981 | Muxfeldt et al. | |
| 4,650,488 A | 3/1987 | Bays et al. | |
| 4,655,771 A | 4/1987 | Wallsten | |
| 4,655,777 A | 4/1987 | Dunn et al. | |
| 4,916,193 A | 4/1990 | Tang et al. | |
| 4,938,763 A | 7/1990 | Dunn et al. | |
| 5,022,399 A | 6/1991 | Biegeleisen | |
| 5,059,211 A | 10/1991 | Stack et al. | |
| 5,085,629 A | 2/1992 | Goldberg et al. | |
| 5,254,105 A | 10/1993 | Haaga | |
| 5,258,042 A * | 11/1993 | Mehta ....................... 600/36 |
| 5,278,202 A | 1/1994 | Dunn et al. | |
| 5,306,286 A | 4/1994 | Stack et al. | |
| 5,324,519 A | 6/1994 | Dunn et al. | |
| 5,370,660 A * | 12/1994 | Weinstein et al. ........... 606/215 |
| 5,382,261 A | 1/1995 | Palmaz | |
| 5,410,016 A | 4/1995 | Hubbell et al. | |
| 5,425,367 A | 6/1995 | Shapiro et al. | |
| 5,443,458 A | 8/1995 | Eury | |
| 5,456,693 A | 10/1995 | Conston et al. | |
| 5,527,337 A | 6/1996 | Stack et al. | |
| 5,573,934 A | 11/1996 | Hubbell et al. | |
| 5,626,863 A | 5/1997 | Hubbell et al. | |
| 5,629,077 A | 5/1997 | Turnlund et al. | |
| 5,665,831 A | 9/1997 | Neuenschwander et al. | |
| 5,674,287 A | 10/1997 | Slepian et al. | |
| 5,749,915 A * | 5/1998 | Slepian ....................... 128/898 |
| 5,752,974 A | 5/1998 | Rhee et al. | |
| 5,766,710 A | 6/1998 | Turnlund et al. | |
| 5,770,645 A | 6/1998 | Stamler et al. | |
| 5,851,508 A | 12/1998 | Greff et al. | |
| 5,858,746 A | 1/1999 | Hubbell et al. | |
| 5,888,546 A | 3/1999 | Ji et al. | |
| 5,894,022 A * | 4/1999 | Ji et al. ....................... 424/422 |
| 5,904,703 A | 5/1999 | Gilson | |
| 5,916,583 A | 6/1999 | Broberg et al. | |
| 5,947,977 A | 9/1999 | Slepian et al. | |
| 6,045,568 A | 4/2000 | Igaki et al. | |
| 6,080,177 A | 6/2000 | Igaki et al. | |
| 6,096,052 A | 8/2000 | Callister et al. | |
| 6,096,070 A | 8/2000 | Ragheb et al. | |
| 6,176,871 B1 | 1/2001 | Pathak et al. | |
| 6,258,084 B1 * | 7/2001 | Goldman et al. ............... 606/32 |
| 6,338,739 B1 | 1/2002 | Datta et al. | |
| 6,379,373 B1 | 4/2002 | Sawhney et al. | |
| 6,387,978 B2 | 5/2002 | Ronan et al. | |
| 6,401,719 B1 | 6/2002 | Farley et al. | |
| 6,409,750 B1 | 6/2002 | Hyodoh et al. | |
| 6,413,272 B1 | 7/2002 | Igaki | |
| 6,423,085 B1 | 7/2002 | Murayama et al. | |
| 6,436,132 B1 | 8/2002 | Patel et al. | |

(Continued)

FOREIGN PATENT DOCUMENTS

WO    WO 94/06460 A    3/1994

(Continued)

OTHER PUBLICATIONS

Abrahams, et al., "Biodegradable polyglycolide endovascular coils promote wall thickening and drug delivery in a rat aneurysm model", Neurosurgery (United States) Nov. 2001, 49 (5) p. 1187-93; discussion 1193-5 (Abstract Only).

(Continued)

*Primary Examiner*—Sharon E. Kennedy
(74) *Attorney, Agent, or Firm*—Knobbe, Martens, Olson & Bear, LLP

(57) ABSTRACT

This invention relates to occlusion of a hollow anatomical structure by inserting an occluding device or occluding material into a hollow anatomical structure or surrounding native tissue.

61 Claims, No Drawings

U.S. PATENT DOCUMENTS

| | | | |
|---|---|---|---|
| 6,443,941 | B1 | 9/2002 | Slepian et al. |
| 6,500,204 | B1 | 12/2002 | Igaki |
| 6,527,801 | B1 | 3/2003 | Dutta |
| 6,548,569 | B1 | 4/2003 | Williams et al. |
| 6,565,601 | B2 | 5/2003 | Wallace et al. |
| 6,569,190 | B2 | 5/2003 | Whalen et al. |
| 6,585,754 | B2 * | 7/2003 | Wallace et al. ............. 623/1.15 |
| 6,605,111 | B2 | 8/2003 | Bose et al. |
| 6,626,939 | B1 | 9/2003 | Burnside et al. |
| 6,632,242 | B2 | 10/2003 | Igaki |
| 6,638,293 | B1 | 10/2003 | Makower et al. |
| 6,645,167 | B1 | 11/2003 | Whalen et al. |
| 6,666,882 | B1 | 12/2003 | Bose et al. |
| 6,676,971 | B2 | 1/2004 | Goupil et al. |
| 6,685,727 | B2 | 2/2004 | Fisher et al. |
| 6,699,272 | B2 | 3/2004 | Slepian et al. |
| 6,703,047 | B2 * | 3/2004 | Sawhney et al. ............. 424/489 |
| 6,726,920 | B1 * | 4/2004 | Theeuwes et al. ........... 424/423 |
| 6,808,518 | B2 * | 10/2004 | Wellman et al. ............. 604/507 |
| 6,818,018 | B1 * | 11/2004 | Sawhney ................. 623/11.11 |
| 7,192,436 | B2 * | 3/2007 | Sing et al. .................... 606/213 |
| 2001/0029398 | A1 | 10/2001 | Jadhav |
| 2001/0044629 | A1 | 11/2001 | Stinson |
| 2001/0056301 | A1 | 12/2001 | Goupil et al. |
| 2002/0019369 | A1 | 2/2002 | Li et al. |
| 2002/0040239 | A1 | 4/2002 | Murayama et al. |
| 2002/0065546 | A1 | 5/2002 | Machan et al. |
| 2002/0099332 | A1 | 7/2002 | Slepian et al. |
| 2002/0106411 | A1 | 8/2002 | Wiron et al. |
| 2002/0165582 | A1 * | 11/2002 | Porter ........................ 606/213 |
| 2002/0177855 | A1 | 11/2002 | Greene et al. |
| 2002/0183830 | A1 | 12/2002 | Su et al. |
| 2002/0188342 | A1 | 12/2002 | Rykhus et al. |
| 2003/0004533 | A1 | 1/2003 | Dieck et al. |
| 2003/0028245 | A1 | 2/2003 | Barclay et al. |
| 2003/0040771 | A1 | 2/2003 | Hyodoh et al. |
| 2003/0045924 | A1 | 3/2003 | Datta et al. |
| 2003/0055488 | A1 | 3/2003 | Igaki |
| 2003/0060874 | A1 | 3/2003 | Igaki |
| 2003/0069629 | A1 | 4/2003 | Jadhav et al. |
| 2003/0086975 | A1 | 5/2003 | Ringeisen |
| 2003/0093111 | A1 | 5/2003 | Ken et al. |
| 2003/0104030 | A1 | 6/2003 | Igaki et al. |
| 2003/0144730 | A1 | 7/2003 | Datta et al. |
| 2003/0149463 | A1 | 8/2003 | Solymar et al. |
| 2003/0149475 | A1 | 8/2003 | Hyodoh et al. |
| 2004/0013703 | A1 | 1/2004 | Ralph et al. |
| 2004/0054372 | A1 | 3/2004 | Corden et al. |
| 2004/0059370 | A1 | 3/2004 | Greene et al. |
| 2004/0082682 | A1 | 4/2004 | Loomis et al. |
| 2004/0098030 | A1 | 5/2004 | Makower et al. |
| 2004/0215231 | A1 * | 10/2004 | Fortune et al. ............. 606/213 |
| 2005/0106119 | A1 | 5/2005 | Brandom et al. |
| 2005/0107867 | A1 | 5/2005 | Taheri et al. |
| 2006/0052822 | A1 | 3/2006 | Mirizzi et al. |
| 2006/0105026 | A1 * | 5/2006 | Fortune et al. ............. 424/443 |
| 2006/0190076 | A1 | 8/2006 | Taheri |
| 2006/0212055 | A1 | 9/2006 | Karabey et al. |
| 2006/0212127 | A1 | 9/2006 | Karabey et al. |
| 2006/0229668 | A1 | 10/2006 | Prestezog et al. |
| 2006/0229669 | A1 | 10/2006 | Mirizzi et al. |
| 2006/0282158 | A1 | 12/2006 | Taheri |
| 2006/0282159 | A1 | 12/2006 | Taheri |
| 2007/0248640 | A1 | 10/2007 | Karabey et al. |

FOREIGN PATENT DOCUMENTS

| | | |
|---|---|---|
| WO | WO 00/32112 | 6/2000 |
| WO | WO 01/68720 | 9/2001 |
| WO | WO 03/051409 | 6/2003 |

OTHER PUBLICATIONS

Bahr, et al., "Vascular anastomosis using a biodegradable device with a heat-shrinking sleeve: a preliminary report", Journal of oral and maxillofacial surgery—official journal of the American Association of Oral and Maxillofacial Surgeons (United States) Dec. 1998, 56 (12), p. 1404-9 (Abstract Only).

Baier, et al., "Photocrosslinked hyaluronic acid hydrogels: natural, biodegradable tissue engineering scaffolds", Biotechnology and bioengineering (United States) Jun. 5, 2003, 82 (5) p. 578-89 (Abstract Only).

Biegeleisen, K., "Use of the venoscope for the treatment of varicose veins", Phlebologie '89, A. Davy, R. Stemmer eds, © 1989 John Libbey Eurotext Ltd, pp. 419-422.

Guan, et al., "Biodegradable poly(ether ester urethane)urea elastomers based on poly(ether ester) triblock copolymers and putrescine: synthesis, characterization and cytocompatibiilty", Biomaterials (England) Jan. 2004, 25 (1) p. 85-96 (Abstract Only).

He, et al., "Assessment of tissue blood flow following small artery welding with an intraluminal dissolvable stent", Microsurgery (United States) 1999, 19 (3) p. 148-52 (Abstract Only).

Hietala, et al., "Biodegradtion of the copolymeric polylactide stent. Long-term follow-up in a rabbit aorta model", Journal of vascular research (Switzerland) Jul.-Aug. 2001, 38 (4) p. 361-9 (Abstract Only).

Hoerstrup, et al., "Tissue engineering of small caliber vascular grafts", European Association for Cardio-thoracic Surgery (England) Jul. 2001, 20 (1) p. 164-9 (Abstract Only).

Hoffman, et al., "Biodegradable synthetic polymer scaffolds for reinforcement of albumin protein solders used for laser-assisted tissue repair", Biomedical sciences instrumentation (United States) 2002, 38 p. 53-8 (Abstract Only).

Izhar et al., "Novel synthetic selectively degradable vascular prostheses: a preliminary implantation study", Journal of surgical research (United States) Feb. 2001, 95 (2) p. 152-60 (Abstract Only).

Joji, et al., "Experimental study of mechanical microvascular anastomosis with new biodegradable ring device", British journal of plastic surgery (England) Oct. 1999, 52 (7) p. 559-64 (Abstract Only).

Kimura, et al., "Evaluation of an absorbable ring for vascular anastomosis", Journal of reconstructive microsurgery (United States) Jul. 1999, 15 (5) p. 331-6 (Abstract Only).

Lee, et al., "Elastic biodegradable poly(glycolide-co-caprolactone) scaffold for tissue engineering", Journal of biomedical materials research (United States) Jul. 1, 2003, 66A (1) p. 29-37 (Abstract Only).

McNally-Heintzelman, et al., "Scaffold-enhanced albumin and n-butyl-cyanoacrylate adhesives for tissue repair: ex vivo evaluation in a porcine model", Biomedical sciences instrumentation (United States) 2003, 39 p. 312-7.

Murayama, et al., "Bioabsorbable polymeric material coils for embolization of intracranial aneurysms: a preliminary experimental study", Journal of neurosurgery (United States) Mar. 2001, 94 (3) p. 454-63 (Abstract Only).

Murayama, et al., "Cellular responses of bioabsorbable polymeric material and Guglielmi detachable coil in experimental aneurysms", Stroke; a journal of cerebral circulation (United States) Apr. 2002, 33 (4) p. 1120-8 (Abstract Only).

Qu, et al., "An absorbable pinned-ring device for microvascular anastomosis of vein grafts: experimental studies", Microsurgery (United States) 1999, 19 (3) p. 128-34 (Abstract Only).

Shi, et al., "Towards tissue engineering of a composite aortic valve", Biomedical sciences instrumentation (United States) 2002, 38 p. 35-40 (Abstract Only).

Su, et al., "Expandable bioresorbable endovascular stent. I. Fabrication and properties", Annals of biomedical engineering (United States) Jun. 2003, 31 (6) p. 667-77 (Abstract Only).

Suzuki, et al., "Simplified hepatic resection utilizing absorbable polyglycolic acid-based tape and other ligature apparatus", Journal of hepato-biliary-pancreatic surgery (Japan) 1998, 5 (3) p. 292-6 (Abstract Only).

International Search Report for corresponding PCT Application No. PCT/US2005/30370 Mailed May 9, 2006.
International Written Opinion for corresponding PCT Application No. PCT/US2005/30370 Mailed May 9, 2006.

Office Action from copending U.S. Appl. No. 11/212,539, filed Aug. 26, 2005.

* cited by examiner

APPARATUS, MATERIAL COMPOSITIONS, AND METHODS FOR PERMANENT OCCLUSION OF A HOLLOW ANATOMICAL STRUCTURE

CROSS-REFERENCE TO RELATED APPLICATIONS

This application claims priority under 35 U.S.C. § 119(e) to U.S. Provisional Application No. 60/605,843, filed Aug. 31, 2004. The above-referenced prior application is incorporated by reference herein in its entirety and is hereby made a portion of this specification.

FIELD OF THE INVENTION

This invention relates to occlusion of a hollow anatomical structure by inserting an occluding device or occluding material into a hollow anatomical structure or surrounding native tissue.

BACKGROUND OF THE INVENTION

The preferred embodiments relate generally to a method and material composition for introduction into a hollow anatomical structure (HAS) with particular relevance to the venous system in the lower extremities. The term "hollow anatomical structure" is a broad term and is used in its ordinary sense, including, without limitation, veins, arteries, gastric structures, coronary structures, pulmonary structures, tubular structures associated with reproductive organs, and the like. Hollow anatomical structures particularly suited to occlusion by the methods of preferred embodiments include veins, preferably veins of the lower extremities, especially veins in the leg.

The human venous system of the lower extremities consists essentially of the superficial venous system and the deep venous system with perforating veins connecting the two systems. The superficial system includes the long or great saphenous vein and the small saphenous vein. The deep venous system includes the anterior and posterior tibial veins which unite to form the popliteal vein, which in turn becomes the femoral vein when joined by the short saphenous vein.

The venous system contains numerous one-way valves for directing blood flow back to the heart. Venous valves are usually bicuspid valves, with each cusp forming a sack or reservoir for blood. Retrograde blood flow forces the free surfaces of the cusps together to prevent continued retrograde flow of the blood and allows only antegrade blood flow to the heart. When an incompetent valve is in the flow path, the valve is unable to close because the cusps do not form a proper seal and retrograde flow of the blood cannot be stopped. When a venous valve fails, increased strain and pressure occur within the lower venous sections and overlying tissues, sometimes leading to additional, distal valvular failure. Two venous conditions or symptoms which often result from valve failure are varicose veins and more symptomatic chronic venous insufficiency.

The resulting condition is progressive and includes: dilation and tortuosity of the superficial veins of the lower limbs, unsightly discoloration, pain, swelling, and possibly ulceration. This failure can also worsen deep venous reflux and perforator reflux. Current treatments of venous insufficiency include surgical procedures such as vein stripping, ligation, RF ablation, laser treatment, vein closure, and vein-segment transplant.

Vein stripping and vein-segment transplant are less-favored treatment options. Vein stripping typically consists of tying off, or ligating, and removal of the saphenous vein. The ligation involves making an incision in the groin and using sutures outside the vein to tie it shut. When the veins are tied off and/or removed, blood flows through the deep veins and back to the heart. This surgery is generally done under general or spinal anesthesia during a hospital stay or on an outpatient basis, depending upon the extent of the procedure. Vein stripping is generally painful and requires a long recovery time. This procedure is less favored and outcomes can be poor. Procedures combining ligation and stripping are sometimes performed, but studies have shown they offer little advantage over stripping alone. Vein segment transplant has been employed in certain organ transplant procedures. However it is not generally employed in the superficial venous system in humans.

Ligation by ablation involves the cauterization or coagulation of vascular lumina using thermal energy applied through a delivery catheter, e.g., electrical energy applied through an electrode device (e.g., a radio frequency or RF device), energy delivered by regular and high-frequency ultrasound, or laser energy. An energy delivery device is typically introduced into the vein lumen and positioned so that it contacts the vein wall. Once properly positioned, the RF, laser, ultrasound, or other energy is applied to the energy delivery device, thereby causing the vein wall to shrink in cross-sectional diameter. A reduction in cross-sectional diameter, for example, from 5 mm (0.2 in) to 1 mm (0.04 in), significantly reduces the flow of blood through the vein and results in an effective ligation. Though not required for effective ligation, the vein wall can completely collapse, thereby resulting in a full-lumen obstruction that blocks the flow of blood through the vein.

SUMMARY OF THE INVENTION

Even with technological advances in the various methods of occlusion, there is a need for a less invasive or non-thermal method for permanent total occlusion of hollow anatomical structures such as incompetent veins. Thus there is an opportunity and a need for less invasive treatments and therapies for venous diseases in the lower extremities. The preferred embodiments provide materials and methods which can be employed to occlude a hollow anatomical structure. Preferably, a bioresorbable (e.g., breaks down and is absorbed by a cell, tissue, or other mechanism within the body) or bioabsorbable (similar to bioresorbable) material is employed to occlude the hollow anatomical structure. Alternatively, a bioerodable (e.g., erodes or degrades over time by contact with surrounding tissue fluids, through cellular activity or other physiological degradation mechanisms), biodegradable (e.g., degrades over time by enzymatic or hydrolytic action, or other mechanism in the body), or dissolvable material is employed. Each of these terms is interpreted to be interchangeable. In certain embodiments, a biocompatible material that is not bioabsorbable, bioerodable, biodegradable, or dissolvable is employed. The bioabsorbable material is preferably placed in the hollow anatomical structure by a minimally invasive method which can be employed for precisely locating the material within the target lumen.

While the methods and materials of preferred embodiments are particularly preferred for use in occluding veins of the lower extremities, they can be employed in occluding other hollow anatomical structures, including, but not limited to: blood vessels such as perforating veins which connect the superficial veins to the deep veins in the leg, truncal superficial veins of the leg (e.g., great saphenous vein, short saphenous vein, and the like), superficial tributary veins of the leg, telangiectasia, internal spermatic veins (varicoceles), ovarian veins, gonadal veins, hemorrhoidal vessels, esophageal varices, fallopian tubes, vas deferens, arteriovenous malformations, arteriovenous fistula networks, aortic aneurysm excluded lumens post AAA graft placement, lumbar arteries, feeding vessels into the aorta to prevent abdominal aortic aneurysm (AAA) graft endoleaks, treatment of sleep apnea, and the like.

Accordingly, in a first aspect an apparatus for occluding a hollow anatomical structure in a patient is provided, the apparatus comprising a bioresorbable material, wherein, upon placement in a hollow anatomical structure, the material blocks fluid flow through the hollow anatomical structure to a degree sufficient to induce a durable occlusion of the hollow anatomical structure.

In an embodiment of the first aspect, the hollow anatomical structure is a blood vessel.

In an embodiment of the first aspect, the material comprises a viscous flow-blocking material.

In an embodiment of the first aspect, the material is configured to be injectable.

In an embodiment of the first aspect, the material is configured to be sufficiently viscous to maintain its position in a hollow anatomical structure with an inside diameter greater than or equal to about 2, 3, 4, or 5 mm or more. The hollow anatomical structure can comprise a blood vessel.

In an embodiment of the first aspect, the material is configured to be sufficiently flowable to flow into a hollow anatomical structure with an inside diameter less than or equal to about 1 or 2 mm. The hollow anatomical structure can comprise a blood vessel.

In an embodiment of the first aspect, the material is selected from the group consisting of collagen, fibrinogen, fibronectin, vitronectin, laminin, thrombin, gelatin, and mixtures thereof, so as to substantially block flow into the hollow anatomical structure by causing clotting and fibrotic tissue occlusion.

In an embodiment of the first aspect, the material is curable in situ upon placement in the hollow anatomical structure.

In an embodiment of the first aspect, the material is configured to undergo a viscosity change in situ after placement in the hollow anatomical structure. The viscosity change can be manifested by at least one process selected from the group consisting of crosslinking, curing, hardening, thickening, and swelling.

In an embodiment of the first aspect, the material is in a form of a sponge. The sponge can have a porous, open-cell configuration. In a preferred embodiment, the sponge has an average pore diameter greater than or equal to about 50 microns, and the porous, open-cell configuration promotes cellular ingrowth upon placement of the sponge in the hollow anatomical structure. Alternatively, the sponge can have a non-porous, closed-cell configuration.

In an embodiment of the first aspect wherein the material is in a form of a sponge, the sponge expands radially in situ to span a cross section of the hollow anatomical structure.

In an embodiment of the first aspect wherein the material is in a form of a sponge, the sponge further comprises an additive selected from the group consisting of sclerosant, venoconstrictor, anti-bacterial agent, drug, anti-inflammatory agent, anti-infective agent, anesthetic, pro-inflammatory agent, cell proliferative agent, tretinoin, procoagulant, and combinations thereof. The procoagulant can be selected from the group consisting of collagen, fibrinogen, fibronectin, vitronectin, laminin, thrombin, gelatin, and mixtures thereof.

In an embodiment of the first aspect, the material is in a form of a plug. The plug can be non-porous, or configured to maintain a cross-sectional size upon placement in the hollow anatomical structure, or is formed in situ in the hollow anatomical structure, or is pre-formed before being placed in the hollow anatomical structure.

In an embodiment of the first aspect, the material is in a form of a sheet, the apparatus further comprising an adhesive disposed on at least one of a first side of the sheet and a second side of the sheet.

In an embodiment of the first aspect, the material is in a form of a tube, the apparatus further comprising an adhesive disposed on at least one of an outer surface of the tube and an inner surface of the tube.

In an embodiment of the first aspect, the material is in a form of a rolled sheet prior to insertion into the hollow anatomical structure, the apparatus further comprising an adhesive disposed on at least one of a first side of the sheet and a second side of the sheet, the sheet having an inserted configuration in which the sheet is at least partially unrolled.

In an embodiment of the first aspect, the material comprises a rod which is configured to swell upon placement in the hollow anatomical structure. The rod can comprise a hydrogel.

In a second aspect, a method for occluding a hollow anatomical structure in a patient is provided, the method comprising the step of placing an occluding material at an occlusion site, whereby an occlusion is formed in the hollow anatomical structure.

In an embodiment of the second aspect, the method further comprises a step of identifying an occlusion site, wherein the step of identifying is conducted before the step of placing an occluding material at the occlusion site.

In an embodiment of the second aspect, the. occluding material comprises a tissue adhesive. The tissue adhesive can be a cyanoacrylate adhesive. Alternatively, the tissue adhesive can be selected from the group consisting of collagen, fibrinogen, fibronectin, vitronectin, laminin, thrombin, gelatin, and mixtures thereof.

In an embodiment of the second aspect, the method further comprises a step of reducing an interior cross-sectional area of the hollow anatomical structure. The area can be reduced by applying a compression to the hollow anatomical structure or by applying a vacuum to an interior of the hollow anatomical structure. In a preferred embodiment, the hollow anatomical structure is a blood vessel, and the area is reduced by administering a venoconstrictor to the patient. The step of reducing an interior cross-sectional area can be conducted before the step of placing an occluding fluid material at the site, or after the step of placing an occluding material at the site.

In an embodiment of the second aspect, the occluding site is near at least one valve in a vein.

In an embodiment of the second aspect, the occluding fluid material comprises a hydrogel, wherein the hydrogel expands in situ to occlude the hollow anatomical structure.

In an embodiment of the second aspect, the step of placing an occluding material comprises the steps of placing at least one temporary occluding device in the hollow anatomical structure adjacent to the site; placing an occluding fluid material at the site adjacent to the temporary occluding device; solidifying or curing the occluding fluid material, whereby an occlusion is formed in the hollow anatomical structure; and removing the temporary occluding device.

In an embodiment of the second aspect, the step of placing an occluding material comprises the steps of placing at least one occluding device in the hollow anatomical structure adjacent to the site, whereby a contiguous occlusion is formed; placing an occluding fluid material at the site adjacent to the occluding device; and solidifying or curing the occluding fluid material, whereby an occlusion is formed in the hollow anatomical structure.

In an embodiment of the second aspect, the occluding material forms a contiguous occlusion.

In an embodiment of the second aspect, the occluding fluid material is placed at at least two separate locations, forming two noncontiguous occlusions. A sclerosant can be placed between the two noncontiguous occlusions.

In an embodiment of the second aspect, the occlusion site is interior to the hollow anatomical structure.

In an embodiment of the second aspect, the occlusion site is exterior to the hollow anatomical structure.

In an embodiment of the second aspect, the hollow anatomical structure is a vein, and the step of placing an occluding material at the site comprises the step of placing a material in a perivenous space surrounding the vein at the occlusion site, whereby an occlusion is formed in the vein. The material can be shrinkable, and the occlusion can be formed by shrinking the material. The material can be collagen, and the step of shrinking can comprise heating the collagen.

In an embodiment of the second aspect, the occluding material comprises collagen, preferably in the form of a plug or a sponge.

In an embodiment of the second aspect, the occluding material comprises an alpha-hydroxy acid, preferably in the form of a plug or a sponge.

In an embodiment of the second aspect, the occluding material comprises a therapeutic agent selected from the group consisting of anti-inflammatory agents, anti-infective agents, anesthetics, pro-inflammatory agents, cell proliferative agents, tretinoin, procoagulants, and combinations thereof.

In an embodiment of the second aspect, the occluding material is in a fluid form that cures in situ to form an occlusion in the hollow anatomical structure.

In an embodiment of the second aspect, the occluding material changes viscosity in situ to form an occlusion in the hollow anatomical structure In an embodiment of the second aspect, the occluding material is placed in the hollow anatomical structure through a needle or a catheter.

In an embodiment of the second aspect, the hollow anatomical structure is a vein, and the method further comprises the step of placing a sclerosant in the vein.

In an embodiment of the second aspect, the occluding material comprises a sclerosant, optionally in combination with dimethyl sulfoxide.

In an embodiment of the second aspect, the occluding material is combined with a sclerosant. The occluding material can be in a form of a sponge, and the sclerosant can be contained on or within the sponge.

In an embodiment of the second aspect, the occlusion is a partial occlusion.

In an embodiment of the second aspect, the occlusion is a complete occlusion.

In an embodiment of the second aspect, the hollow anatomical structure is part of the superficial human venous system of the lower extremities.

In an embodiment of the second aspect, the hollow anatomical structure is a vein selected from the group consisting of the great saphenous vein, the small saphenous vein, a perforating vein which connects superficial veins to deep veins in the leg, and a superficial tributary vein of the leg.

In an embodiment of the second aspect, the hollow anatomical structure is selected from the group consisting of telangiectasia, internal spermatic vein, ovarian vein, gonadal vein, hemorrhoidal vessel, esophageal varices, fallopian tube, vas deferens, arteriovenous malformation, arteriovenous fistula network, aortic aneurysm excluded lumens post abdominal aortic aneurysm graft placement, lumbar artery, and feeding vessel into the aorta.

In an embodiment of the second aspect, the step of identifying an occlusion site in a hollow anatomical structure utilizes an identification method selected from the group consisting of ultrasound, compression, palpation, endoscopy, fluoroscopy, and use of contrast media.

In a third aspect, a kit for use in forming an occlusion in a hollow anatomical structure in a patient is provided, the kit comprising an occluding material comprising a biocompatible injectable fluid or bioabsorbable injectable fluid, and instructions for placing an occluding material at the site, whereby an occlusion is formed in the hollow anatomical structure. The kit can further include instructions for identifying an occlusion site.

In an aspect of the third embodiment, the kit further comprises a delivery device for placing the occluding material at the occlusion site, the delivery device comprising a needle or a catheter.

DETAILED DESCRIPTION OF THE PREFERRED EMBODIMENT

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Methods for occluding a hollow anatomical structure in a patient or subject using an occluding device or occluding material are provided. The terms "subject" and "patient" as used herein, refer to animals, such as mammals. For example, mammals contemplated by the include humans, primates, dogs, cats, sheep, cattle, goats, pigs, horses, mice, rats, rabbits, guinea pigs, and the like. The terms "subject" and "patient" are used interchangeably.

The terms "occluding device" and "occluding material" as used herein, are broad terms and are used in their ordinary sense, including, without limitation, a substance or device that is capable of occluding or causing occlusion of a hollow anatomical structure. Occlusion can be "acute" (i.e., complete blockage, or 100% volume filling) or "partial" (i.e., less than complete blockage, or less than 100% volume filling). Occlusion can include blocking or inhibiting blood flow to a degree sufficient to relieve patient symptoms, inducing clotting or tissue ingrowth, causing a durably fibrotic occlusion, or occluding in other fashions, either directly or indirectly. Occluding materials or occluding devices can be formed or fabricated ex situ, or formed in situ (e.g., by curing of a prepolymer or uncured polymer). Occluding can be achieved directly by the occluding material or induced indirectly by the occluding material. The term "occluding material" as employed herein, includes prepolymers, uncured polymers, unsolidifed materials, as well as occluding materials inserted into a patient in precured or solidified form. Bioabsorbable materials are particularly preferred occluding materials.

Occluding can include, but is not limited to, blocking by insertion of a plug or other structure into the hollow anatomical structure that prevents or inhibits flow therethrough, adhering opposite walls of the hollow anatomical structure together so as to prevent or inhibit flow therethrough, compressing the walls of the hollow anatomical structure together so as to prevent or inhibit flow therethrough, or initiating a physiological reaction to an applied force or substance (e.g., energy, chemicals, drugs, physical contact, pressure or the like) that causes flow through the hollow anatomical structure to be inhibited or prevented (e.g., formation of an organized thrombus, or growth of connective tissue). Occlusion can be immediate, or onset of occlusion can be delayed. Occlusion can be partial (permitting a reduced flow through the hollow anatomical structure) or complete (permitting no flow through the hollow anatomical structure). Occlusion can be permanent or temporary. Occlusion can result in physical change or damage to the hollow anatomical structure (e.g., sclerosis), or can block the hollow anatomical structure without substantial physical change (e.g., a biocompatible plug). The mechanisms by which occlusion can occur include but are not limited to formation of a wound or damage to tissue, expansion of the occluding device or occluding material, release of a chemical (e.g., a sclerosant or inflammatory agent) from the occluding device or occluding material, venoconstriction, compression, and ligation. Other mechanisms, forms, and effects of occlusion will be appreciated by those of skill in the art.

Occluding Materials

The use of organic materials and polymers in medical application is widely known and accepted in the medical field. Representative examples of such materials include absorbable materials composed of purified connective tissue (collagen) derived from the serosal layer of cattle (bovine) intestines, as well as synthetic materials such as VICRYL™ polymer manufactured by Johnson & Johnson/Ethicon. Further advances in biodegradable and bioabsorbable materials have led to breakthrough developments in the stent field with the primary intention of maintaining patency after placement. Stents have been developed for coronary artery disease (e.g., plaque in the arteries, associated with myocardial infarction/heat attack), or aneurisms. Stents have also been employed in urology to maintain an opening in a urethra that's swollen shut, for example, as a complication of benign prostate hyperplasty. Stent grafts with bioactive coatings are described in U.S. Publ. No. 2002/0065546 A1 to Machan, et al., the contents of which are hereby incorporated by reference in their entirety.

Any suitable material can be employed to occlude the hollow anatomical structure. Generally, non-rigid materials are preferred. However, in certain embodiments it can be advantageous to employ a rigid material. The materials are preferably flexible or deformable, or in fluid form, such as a highly viscous fluid. A fluid that solidifies or cures to a solid form (for example, a prepolymer) can also be employed. The material is preferably bioabsorbable materials that can be fabricated into a desired form (e.g., sponge, matrix, powder, plug, rod, fibrous mass, or the like) for insertion into the hollow anatomical structure, or which can be formed in place (e.g., inserted in fluid or other form, then cured by light, heat, exposure to physiological conditions (pH), water, bodily fluids, or solvent). A suitable size and shape of the material is selected according to the hollow anatomical structure to be occluded. In an area of low venous blood flow, a structure which is slightly larger than the inner diameter of the vessel is generally preferred. For applications wherein permanent occlusion of vessels (e.g., arteries) subjected to high pressures is desired, a structure of higher compression modulus and larger expanded size relative to the inner diameter of the lumen is typically preferred. The shape of the material can also be tailored to fit the need of a given application. A spherical, cylindrical, rod, conical, oval, rolled, helical, coiled or other shape can be employed, as desired. The shape can be solid or porous. The shape can comprise a composite of two or more materials with different bioabsorption rates, different biodegradation rates, solubilities, porosities, strengths, rigidities, or the like. Likewise, materials of different forms (liquid, solid, gel, fibrous mass, and the like) can be used in combination.

The occluding device or material is preferably a bioabsorbable material. Bioabsorbable materials employed to occlude a hollow anatomical structure are preferably solid and flexible. The bioabsorbable material can be in the form of a sponge or foam, or can comprise a contiguous block of material lacking void spaces. The bioabsorbable material can comprise a single component, or can be fabricated as a composite material constructed from two or more components. In one embodiment, the occluding device comprises a thin sheet with adhesive on both sides. Alternatively, adhesion between the walls of the hollow anatomical structure can be provided by blood clotting or blood clotting promoting agents, rather than a conventional tissue adhesive.

In embodiments wherein an adhesive sheet is employed, the sheet is placed in the hollow anatomical structure and adheres opposite walls of the hollow anatomical structure together when external compression or vacuum is applied to the hollow anatomical structure. Alternatively, the occluding device can include a mechanical or chemical abrasive. The abrasive causes endothelial cell destruction when it contacts the walls of the hollow anatomical structure, facilitating the occlusion process. Alternatively, the bioabsorbable material can be fabricated such that it possesses an abrasive surface. The bioabsorbable material can be fabricated to exhibit micromotion in situ, to facilitate abrasion against the walls of the hollow anatomical structure. Preferably, the occluding device or occluding material provokes an inflammatory response, causing a wound. This initiates a fibrotic response from the remaining tissue, or initiates the body's natural healing response, or causes the wound healing cascade to initiate. The degree of inflammatory response can be controlled by altering material properties, the amount of material, amount of active agent. However, in other embodiments it can be preferred that the occluding device or occluding material not provoke an inflammatory response.

Bioabsorbable materials suitable for use in preferred embodiments preferably exhibit an absorption period of from about three days or less to one year or more, preferably from about 1 week to 2, 3, 4, 5, 6, 7, 8, 9, 10, or 11 months, more preferably from about 1 week to about 2, 3, 4, 5, or 6 weeks. Rigid materials can be acceptable for use in those indications wherein the material does not cause pain upon movement or inhibit movement. When ease of movement is desirable (e.g., in the occlusion of veins in the lower extremities), the material is preferably flexible. The material is preferably not excessively brittle if exposed to forces that could shatter it so as to destroy any occluding function. However, if external forces after placement are minimal, then materials with some degree of brittleness can be suitable for use. For fluid occluding materials, the viscosity is preferably low enough so as to enable placement of the material, e.g., by catheter or needle), but is preferably high enough such that the material does not exhibit excessive migration. In certain embodiments, it is desirable to employ a fluid material that possesses a degree of "stickiness" or demonstrates adhesive properties.

Such materials can include naturally occurring materials or materials derived from natural sources, or synthetic materials.

Examples of biodegradable polymers which can be used include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyhydroxyalkanoates (PHAs), polyalkylene oxalates, polyalkylene succinates, poly(malic acid), poly(amino acids), polyvinylpyrrolidone, polyethylene glycol, polyhydroxycellulose, chitin, chitosan, and copolymers, terpolymers, or combinations or mixtures of the above materials, with or without added components. Suitable biocompatible and bioabsorbable polymers are described in U.S. Pat. No. 6,423,085 to Murayama et al., and U.S. Pat. No. 6,676,971 to Goupil, et al., the contents of which are hereby incorporated by reference in their entirety. Proteins such as collagen, fibrinogen, fibronectin, vitronectin, laminin, thrombin, and gelatin can also be employed.

Other suitable materials include alpha-hydroxy acids, such as polyglycolides, polylactides, and copolymers of lactic acid and glycolic acid). Poly(lactic-glycolic acid) (PLGA) is a suitable material. It is a synthetic absorbable copolymer of glycolide and lactide marketed under the trade name VICRYL™ (a Polyglactin 910 manufactured by Ethicon, a division of Johnson & Johnson of Somerset, N.J.). It is absorbed though enzymatic degradation by hydrolysis Gelatin is an absorbable material often used in surgical procedures to arrest venous or oozing bleeding. In sponge form, gelatin adheres to tissue and absorbs approximately forty-five times its own weight in fluids. Gelatin is typically absorbed within three to five weeks after implantation into the body.

Collagen is a bioabsorbable material, typically obtained from a processed animal source such as bovine corium(hide), bovine tendon, or porcine skin. Reprocessed insoluble collagen from animal sources is commercially available in the form of sponges or non-woven webs. The collagen can formed into a structure of suitable size and shape to occlude the hollow anatomical structure, for example, a plug. Sponge-like porous plugs with pore diameters greater than 50 microns are preferred for promoting cellular ingrowth. A dry, highly compressed collagen plug when fully hydrated expands to several times its compressed size within a short period of time upon contact with a bodily fluid, tightly affixing itself to a particular location within a blood vessel. Preferred collagen materials are marketed as COLLASTAT® Hemostatic Sponge (Vitaphore Corp.), VITACOL™ (Vitaphore Corp.), and Semex Collagen Powder (Semex Medical, Inc.). The collagen can be crosslinked with formaldehyde, glutaraldehyde, or other suitable agents to increase the strength or compression modulus of the material and to slow its bioerosion in vivo. Particularly preferred collagen plugs are disclosed in U.S. Pat. No. 5,456,693 to Conston, et al., the contents of which are hereby incorporated by reference in their entirety.

Polyglycolic acid (PGA) is a synthetic absorbable polymer. Polyglycolic acid, which exhibits hydrolytic susceptibility, is typically absorbed within a few months post-implantation. Polylactide (PLA) is prepared from the cyclic diester of lactic acid (lactide) by ring opening polymerization for high molecular weight polymers or by direct condensation for low molecular weight polymers. Lactic acid exists as two optical isomers or enantiomers. The L-enantiomer occurs in nature, and a D,L racemic mixture results from the synthetic preparation of lactic acid. The time required for poly-L-lactide to be absorbed by the body is relatively long compared to other bioabsorbable materials. Foams made from bioresorbable PLAs and/or PGAs are particularly preferred.

Polydioxanone can be suitable for use in preferred embodiments, as can polycaprolactone, which is absorbed very slowly in vivo.

Poly-b-hydroxybutyrate is a biodegradable polymer that occurs in nature and can easily be synthesized in vitro. Poly-b-hydroxybutyrate is also melt processable. Copolymers of hydroxybutyrate and hydroxyvalerate exhibit more rapid degradation than does pure poly-b-hydroxybutyrate.

Synthetic absorbable polyesters containing glycolate ester linkages are suitable for use as substrates in preferred embodiments. Similar copolymers prepared using dioxanone instead of glycolide can also be employed, as can poly(amino acids).

A bioabsorbable material suitable for use in preferred embodiments is marketed under the tradename ATRIGEL® by Atrix Laboratories. ATRIGEL® consists of biodegradable polymers dissolved in biocompatible carriers, specifically, polylactic acid dissolved in N-methyl-2-pyrrolidone solvent. Pharmaceuticals can be blended into ATRIGEL® at the time of manufacturing or can be added later by the physician at the time of use. When the liquid product is injected or placed in accessible tissue sites through a cannula, displacement of the carrier with water in the tissue fluids causes the polymer to precipitate to form a solid film or implant. Any drug or other substance (e.g., a sclerosant) encapsulated within the implant is then released in a controlled manner as the polymer matrix biodegrades with time. Depending upon the patient's medical needs, the ATRIGEL® system can deliver small molecules, peptides, proteins, or other substances over a period ranging from days to months.

Catgut, siliconized catgut, and chromic catgut are suitable for use in certain embodiments. Other naturally occurring materials include, but are not limited to, starches, cellulose, acetates, and thrombin. Selected natural materials can provoke a heightened inflammatory response, which can be desirable for facilitating the occlusion process. However, synthetic materials are generally preferred over natural materials for occluding the hollow anatomical structure due to their generally predictable performance.

While bioabsorbable occluding materials are generally preferred, in certain embodiments biocompatible materials that are not also bioabsorbable or biodegradable can be employed. For example, medical grade polyurethane sponges or foams such as HYPOL™ (The Dow Chemical Co.), can be employed. Such urethane foams have good memory characteristics and a higher compression modulus in water than a collagen sponge of similar solids content. The polyurethane plugs can be employed without modification, or can be impregnated with collagen or crosslinked collagen.

2-Cyanoacrylic esters, more commonly referred to as cyanoacrylates, are suitable for use in certain embodiments for occluding a hollow anatomical structure. Cyanoacrylates are hard glass resins that exhibit excellent adhesion to high energy surfaces, such as tissue. The excellent adhesive properties of cyanoacrylate polymers arises from the electron-withdrawing characteristics of the groups adjacent to the polymerizable double bond, which accounts for both the extremely high reactivity or cure rate, and their polar nature, which enables the polymers to adhere tenaciously to many diverse substrates. The ability of cyanoacrylates to rapidly cure and bond to skin makes them particularly well suited for use as medical adhesives. Cyanoacrylate adhesives suitable for use as medical adhesives include octyl 2-cyanoacrylate marketed as DERMABOND™ topical skin adhesive by Ethicon, Inc., a Johnson & Johnson Company, of Somerville, N.J., and butyl cyanoacrylate marketed as VETBOND™ by World Precision Instruments, Inc. of Sarasota, Fla.

Cyanoacrylate adhesives for medical and veterinary use generally include the longer alkyl chain cyanoacrylates, including the butyl and octyl esters. Octyl cyanoacrylates are the most widely used cyanoacrylate adhesive for tissue sealing. When bonding to tissue, octyl cyanoacrylates are four times stronger and less toxic than butyl cyanoacrylate. However, butyl cyanoacrylate is sometimes preferred for sealing deeper lacerations because it breaks down more easily and can be absorbed by the tissue more quickly than octyl cyanoacrylate. Cyanoacrylate liquid monomers polymerize nearly instantaneously via an anionic mechanism when brought into contact with any weakly basic or alkali surface. Even the presence of a weakly basic substance such as moisture is adequate to initiate the curing reaction. The curing reaction proceeds until all available monomer has reacted or until it is terminated by an acidic species. The time of fixture for cyanoacrylate occurs within several seconds on strongly catalytic surfaces to several minutes on noncatalytic surfaces. Surface accelerators or additives enhancing the curing rate may be used to decrease the time of fixture on noncatalytic surfaces. The cyanoacrylate adhesive can be formulated into a bioerodable material by inclusion of a pore forming agent (e.g., an agent that is soluble in tissue fluids, and that dissolves to leave pores and fissures in the polymerized mass).

Other suitable adhesives can include epoxies, UV-activated adhesives, and heat-activated adhesives, as are known in the art. Suitable biocompatible materials for use as occluding devices or materials, or in the preparation of occluding devices, can include polysilicones, polyurethanes, and the like.

In certain embodiments, it can be preferred to employ a hydrogel as an occluding material. Hydrogels form a specific class of polymeric biomaterials, and are generally defined as two- or multicomponent systems consisting of a three-dimensional network of polymer chains and water that fills the space between macromolecules. Depending on the properties of the polymer or polymers used, as well as on the nature and density of the network joints, such structures in an equilibrium can contain various amounts of water; typically in the swollen state the mass fraction of water in a hydrogel is much higher than the mass fraction of polymer. Two general classes of hydrogels can be defined: physical gels (pseudogels), where the chains are connected by electrostatic forces, hydrogen bonds, hydrophobic interactions or chain entanglements (such gels are non-permanent and usually they can be converted to polymer solutions by heating); and chemical (true, permanent) hydrogels with covalent bonds linking the chains.

The polymers used as hydrogels in the preferred embodiments preferably exhibit at least moderate hydrophilic character. In practice, to achieve high degrees of swelling, it is common to use synthetic polymers that are water-soluble when in non-crosslinked form. Typical simple materials employed as hydrogels include but are not limited to poly (ethylene oxide), poly(vinyl alcohol), polyvinylpyrrolidone, and poly(hydroxyethyl methacrylate). There are also natural polymers, such as polysaccharides, that can form hydrogels. Hydrogels commonly employed in soft contact lenses, wound dressings, drug-delivery systems, and the like, can be suitable for use in preferred embodiments. Hydrogels typically exhibit good biocompatibility in the contact with blood, body fluids, and tissues. Hydrogels can be employed that are capable of reacting to various environmental stimuli as temperature, pH, ionic strength, solute concentration, electric field, light, sound, and the like. Hydrogels suitable for use in preferred embodiments include cyclodextrins such as those described in U.S. Publ. No. 2002/0019369 A1 to Li, et al., the contents of which are hereby incorporated by reference in their entirety.

Hydrogels can be employed in any suitable shape or form, e.g., injectable liquid, or rod, plug, or other solid shape. A hydrogel in the form of a suitably sized swellable rod is particularly preferred for use in forming an occlusion in a hollow anatomical structure.

Additional Components in Bioabsorbable Material

In a preferred embodiment, the occluding device or occluding material incorporates additional components. Such components can include physiologically active materials, including but not limited to therapeutic agents, analgesic agents, anti-infectives, preservatives, binders, fillers, excipients, sclerosants, venoconstrictors, and the like. In a particularly preferred embodiment, the occluding device or occluding material is coated with a sclerosant, a venoconstrictor, or both a sclerosant and a venoconstrictor. In other embodiments, the occluding device or occluding material is coated with a tissue adhesive, optionally combined with a sclerosant, a venoconstrictor, or both a sclerosant and a venoconstrictor. While it is generally preferred to incorporate sclerosants, venoconstrictors, or tissue adhesives as coatings on the occluding device or occluding material, in other embodiments such additional components can be mixed or blended with the occluding material.

Sclerosants

In a preferred embodiment, a sclerosant is employed with the methods and materials for occluding hollow anatomical structures as described herein. Sclerosants can include those conventionally employed in sclerotherapy to close veins. Detergent sclerosants work by a mechanism known as protein theft denaturation, in which an aggregation of detergent molecules forms a lipid bilayer in the form of a sheet, a cylinder, or a micelle, which then disrupts the cell surface membrane and removes proteins from the cell membrane surface. The loss of protein causes a delayed cell death. Unlike many other agents, the detergent sclerosants do not cause hemolysis, nor do they provoke direct intravascular coagulation. Sodium morrhuate is a detergent sclerosant made up of a mixture of saturated and unsaturated fatty acids extracted from cod liver oil. It is a biological extract rather than a synthetic preparation, and the composition can vary from lot to lot, and a significant fraction of its fatty acids and alcohols are of chain lengths that probably do not contribute to its effectiveness as a sclerosant. It is unstable in solution, causes extensive cutaneous necrosis if extravasated, and has been responsible for many cases of anaphylaxis. Ethanolamine oleate, a synthetic preparation of oleic acid and ethanolamine, has weak detergent properties because its attenuated hydrophobic chain lengths make it excessively soluble and decrease its ability to denature cell surface proteins. High concentrations of the drug are necessary for effective sclerosis, and its effectiveness in esophageal varices depends upon mural necrosis. Allergic reactions are uncommon, but there have been reports of pneumonitis, pleural effusions, and other pulmonary symptoms following the injection of ethanolamine oleate into esophageal varices. It has a high viscosity that makes injection difficult, a tendency to cause red cell hemolysis and hemoglobinuria, the occasional production of renal failure at high doses, the possibility of pulmonary complications, and a relative lack of strength compared with other available sclerosants. Sodium tetradecyl sulfate is a synthetic long chain fatty acid that is sold for medical use as a solution of up to 3% concentration with 2% benzoyl alcohol used as a stabilizer. It is effective as a venous sclerosing agent in concentrations from 0.1% to 3%, and has proven to be a reliable, safe, and effective sclerosant. The principal clinical problems with the drug are a tendency to cause hyperpigmentation in up to 30% of patients, a significant incidence of epidermal necrosis upon extravasation, and occasional cases of anaphylaxis.

Polidocanol (hydroxy-polyethoxy-dodecane) is a synthetic long-chain fatty alcohol employed as a sclerosant. Polidocanol is painless upon injection. It does not produce necrosis if injected intradermally, and has been reported to have a very low incidence of allergic reactions. Occasional anaphylactic reactions have been reported. In some patients it may produce hyperpigmentation, although to a lesser extent than many other agents. Telangiectatic matting after sclerotherapy with polidocanol is as common as with any other agent. Scleremo, a compound of 72% chromated glycerin, is a polyalcohol that is a very weak sclerosant and is principally useful in the sclerosis of small vessels. Its principal advantage is that it rarely causes hyperpigmentation or telangiectatic matting, and that it very rarely causes extravasation necrosis. The main problems with scleremo are that it is hard to work with because it is extremely viscous, that it can be quite painful on injection, that the chromate moiety is highly allergic, and that it has occasionally been reported to cause urethral colic and hematuria.

Strong solutions of hypertonic saline and other salt solutions are part of a class of solutions that are often referred to as osmotic sclerosants. These solutions have long been regarded as causing endothelial death by osmotic cellular dehydration. Hypertonic solutions of saline as agents for sclerotherapy can be prepared as 20% or 23.4% solutions. The principal advantage of saline is the fact that it is a naturally occurring bodily substance with no molecular toxicity. Because of effects of dilution, it is difficult to achieve adequate sclerosis of large vessels without exceeding a tolerable salt load. It can cause significant pain on injection, and significant cramping after a treatment session. If extravasated, it almost invariably causes significant necrosis. Because it causes immediate red blood cell hemolysis and rapidly disrupts vascular endothelial continuity, it is prone to cause marked hemosiderin staining that is not very cosmetically acceptable. Sclerodex is a mixture of 25% dextrose and 10% sodium chloride, with a small quantity of phenethyl alcohol. A primarily hypertonic agent, its effects are similar to those of pure hypertonic saline, but the reduced salt load offers certain benefits. Like pure hypertonic saline, it is somewhat painful on injection, and epidermal necrosis continues to be the rule whenever extravasation occurs. Polyiodinated iodine is a mixture of elemental iodine with sodium iodide, along with a small amount of benzyl alcohol. It is rapidly ionized and rapidly protein-bound when injected and most likely works by localized ionic disruption of cell surface proteins in situ. In vivo conversion of ionized iodine to iodide renders the solution ineffective as a sclerosant, thus localizing the sclerosing effects to the immediate area of injection. It has a high tendency to cause extravasation necrosis, its limited effectiveness at a distance from the injection site, and the risks of anaphylaxis and of renal toxicity that are associated with ionic iodinated solutions.

Other chemical sclerosants exist that act by a direct or indirect chemical toxicity to endothelial cells: by poisoning some aspect of cellular activity that is necessary for endothelial cell survival. Such agents are less useful to the extent that they also poison other bodily cells. They also lack another of the key attributes of a good sclerosant: they remain toxic to some degree even after extreme dilution, so that there is no real threshold below which injury will not occur.

In a preferred embodiment, occlusion of a hollow anatomical structure at either end is achieved as described above, and the open space in between the occlusions is filled with a sclerosant. This occlusion method is particularly preferred for occluding varicose veins.

In certain embodiments it is preferred to inject a sclerosant directly into the hollow anatomical structure. However, in certain embodiments it can be desired to apply sclerosant by placing a sponge or fibrous mass to which sclerosant has been applied in the hollow anatomical structure.

Venoconstrictors

In a preferred embodiment, a venoconstrictor is employed with the methods and materials for occluding hollow anatomical structures as described herein. Venoconstrictors include, but are not limited to sodium, potassium, epinephrin, norepinephrine, phenylephrine, vasopressin, noradrenaline, and the like.

In a preferred embodiment, a venoconstrictor is combined with the bioabsorbable material, or is applied or administered separately from the bioabsorbable material. For example, the venoconstrictor can be injected first, endovenously, then the bioabsorbable material can be injected endovenously. Alternatively, the venoconstrictor can be injected first, perivenously, then the bioabsorbable material can be injected endovenously.

The venoconstrictor reduces the volume of the vein, such that less material is required to occlude the vein. The vein can be easier to fill, and better adhesion of the bioabsorbable occlusive agent, or tissue adhesive, is observed. Sodium-potassium mixtures are particularly preferred venoconstrictors. However, any suitable venoconstrictor can be employed.

Medicaments and Other Auxiliary Substances

Any suitable physiologically active substance or excipient can be employed in connection with the occluding devices or materials of preferred embodiments. Preferred substances include, but are not limited to, anti-inflammatory agents, anti-infective agents, anesthetics, pro-inflammatory agents, preservatives, cell proliferative agents, tretinoin, procoagulants, fillers, binders, surfactants, and the like.

Suitable anti-inflammatory agents include but are not limited to, for example, nonsteroidal anti-inflammatory drugs (NSAIDs) such aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, dexamethasone, silver, silver complexes, and silver salts.

Anti-infective agents may include, but are not limited to, anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin, benzylpenicillin), tetracyclines (doxycycline, minocycline, tetracycline), bacitracin; rifampicin; lincomycin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim. Anti-infective agents such as silver, silver ions, colloidal silver, silver sulfadiazine, and silver nitrate can also be employed.

Anesthetics may include, but are not limited to ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine.

Other substances that can be incorporated into occluding materials or occluding devices of preferred embodiments include various pharmacological agents, excipients, sclerosants, venoconstrictors, and other substances well known in the art of pharmaceutical formulations. Other substances include, but are not limited to, antiplatelet agents, anticoagulants, coagulants, ACE inhibitors, cytotoxic agents, ionic and nonionic surfactants (e.g., PLURONIC™, TRITON™), detergents (e.g., polyoxyl stearate, sodium lauryl sulfate), emulsifiers, demulsifiers, stabilizers, aqueous and oleaginous carriers (e.g., white petrolatum, isopropyl myristate, lanolin, lanolin alcohols, mineral oil, sorbitan monooleate, propylene glycol, cetylstearyl alcohol), solvents, preservatives (e.g., methylparaben, propylparaben, benzyl alcohol, ethylene diamine tetraacetate salts), thickeners (e.g., pullulin, xanthan, polyvinylpyrrolidone, carboxymethylcellulose), plasticizers (e.g., glycerol, polyethylene glycol), antioxidants (e.g., vitamin E), buffering agents, and the like.

The auxiliary substances can be employed in connection with the occluding device or material in any suitable manner. For example, one or more auxiliary substances can be mixed directly into an occluding material, coated on or otherwise applied to an occluding device, impregnated into an occluding device, placed in a hollow anatomical structure prior to placement of the occluding device or material, applied to a portion of the hollow anatomical structure after placement of the occluding device or material, or any combination thereof. Different auxiliary substances can be employed in different manners. Likewise, a single auxiliary substance can be employed in different manners, or different auxiliary substances can all be employed in the same manner.

In preferred embodiments, auxiliary substances can be incorporated into the occluding material or occluding device in encapsulated form. Certain substances may contain reactive groups that prematurely initiate curing of an uncured bioabsorbable material. Other substances may be sensitive to the components of the occluding material and as a result may undergo adverse chemical reactions or become less active or nonactive. Alternatively, controlled or delayed release of the agent from an occluding material may be desired. Microencapsulation is an effective technique to avoid undesired chemical interaction between auxiliary substances and occluding materials, and to provide controlled release of auxiliary substances from an occluding material.

In a preferred embodiment, the auxiliary substances are entrapped into hydrophilic gelatin microcapsules and mixed with the uncured or fluid occluding material. However, any suitable material can be employed for the microcapsule. Typical encapsulating materials include, but are not limited to, gum arabic, gelatin, ethylcellulose, polyurea, polyamide, aminoplasts, maltodextrins, and hydrogenated vegetable oil. Particularly preferred encapsulating materials include, but are not limited to, gum arabic, gelatin, diethylcellulose, maltodextrins, and hydrogenated vegetable oils. Gelatin is particularly preferred because of its low cost, biocompatibility, and the ease with which gelatin shell microcapsules may be prepared. In certain embodiments, however, other shell materials may be preferred. The optimum shell material may depend upon the particle size and particle size distribution of the filling material, the shape of the filling material particles, compatibility with the filling material, stability of the filling material, and the rate of release of the filling material from the microcapsule.

Microencapsulation techniques typically involve the coating of small solid particles, liquid droplets, or gas bubbles with a thin film of a material, the material providing a protective shell for the contents of the microcapsule. Microcapsules suitable for use in the preferred embodiments may be of any suitable size, typically from about 1 µm or less to about 1000 µm or more, preferably from about 2 µm to about 50, 60, 70, 80, 90, 100, 200, 300, 400, 500, 600, 700, 800, or 900 µm, and more preferably from about 3, 4, 5, 6, 7, 8, or 9 µm to about 10, 15, 20, 25, 30, 35, 40 or 45 µm. In certain embodiments, it may be preferred to use nanometer-sized microcapsules. Such microcapsules may range from about 10 nm or less up to less than about 1000 nm (1 µm), preferably from about 10, 15, 20, 25, 30, 35, 40, 45, 50, 60, 70, 80, or 90 nm up to about 100, 200, 300, 400, 500, 600, 700, 800, or 900 nm. While in most embodiments a solid phase substance is encapsulated, in certain embodiments it may be preferred to incorporate a liquid or gaseous substance. Liquid or gas containing microcapsules can be prepared using conventional methods well known in the art of microcapsule formation, and such microcapsules may be incorporated into the adhesives of the preferred embodiments. In certain embodiments, it may be preferred that the microcapsules contain a plurality of substances, e.g., a plurality of medicaments, or a plurality of substances not including medicaments or pharmaceutical formulations.

The occluding materials or occluding devices of preferred embodiments are preferably sterile. The occluding materials can contain any desired substances, including auxiliary substances such as are described in standard texts, such as "Remington: The Science and Practice of Pharmacy", Lippincott Williams & Wilkins; 20th edition (June 1, 2003) and "Remington's Pharmaceutical Sciences," Mack Pub. Co.; $18^{th}$ and $19^{th}$ editions (December 1985, and June 1990, respectively), incorporated herein by reference in their entirety.

Controlled release formulations can be employed wherein the auxiliary substances are incorporated into an occluding material that permits release by, e.g., diffusion or leaching mechanisms. Slowly degenerating substances can also be incorporated into the occluding material so as to facilitate bioabsorption or bioerosion. Other delivery systems can include timed release, delayed release, or sustained release delivery systems for one or more components of the occluding material. It is generally preferred that a material is released over a period of from about an hour or less to about a month or more, more preferably over a period of from about 2, 3,4, 5, 6, 7, 8, 9, 10, 11, 12, 13, 14, 15, 16, 17, 18, 19, 20, 21, 22, 23, or 24 hours to about 2, 3, 4, 5, 6, 7, 8, 9, 10, 11, 12, 13, 14, 15, 16, 17, 18, 19, 20, 21, 22, 23, 24, 25, 26, 27, 28, 29, or 30 days.

Solvents

In certain embodiments, it can be desirable to use a solvent or penetration enhancer, e.g., dimethyl sulfoxide (DMSO), ethanol, oleic acid, propylene glycol, or the like, in connection with the occluding material or one or more of any additional components present. For example, the solvent or penetration enhancer can be mixed with an occluding material or a sclerosant to enhance adsorption or uptake of the material or sclerosant by the adjacent tissue. If the occluding device is a sponge or some other porous form, the device can be soaked in or permeated by the solvent or penetration enhancer (either in pure form or diluted by a suitable solvent).

General Methodology

The general methodology employed to occlude a hollow anatomical structure typically involves identifying a site to be occluded, and placing an occluding device or occluding material at the site. In a preferred method, the site at which the occluding device or material is placed is identified by any suitable method. Suitable methods include, but are not limited to, ultrasound, compression, endoscopy, fluoroscopy, other methods utilizing contrast media, and the like. Once the placement site is identified, the occluding device or material is placed or inserted either within or external to the hollow anatomical structure. Placement can be achieved using any suitable device, including but not limited to a needle, a catheter, guide wire, a trocar, other intravascular delivery devices, cannula, and the like. Placement methods include but are not limited to insertion, manual injection, controlled feed, controlled pull, delivery through a sheath, or delivery through any other suitable tubular or hollow member, pneumatic, electrical, and the like.

Generally, the desired site within a hollow anatomical structure, such as a blood vessel, is accessed with a catheter. For small diameter torturous vessels, the catheter can be guided to the site by the use of a guide wire. Once the site has been reached, the catheter lumen is cleared by removing the guide wire. An occluding material can then be inserted through the catheter and cured or solidified in situ. For placement of plugs or other solid occluding materials, the material can be loaded by a pusher wire. The material can be attached to the end of the pusher wire via a cleavable joint (e.g., a joint that is severable by heat, electrolysis, electrodynamic activation, or the like) or a mechanical joint that permits the material to be detached from the distal end of the pusher wire by mechanical manipulation. Alternatively, the material can be free and detached from the pusher wire, and simply pushed through the catheter and expelled from the distal end of the catheter at the desired location. Also, the material or device can be exposed and placed through removing an outer sheath.

If the occluding device is preformed, it can immediately occlude the vessel upon placement. In certain embodiments, wherein the occluding device is a sponge or other expanding material, the device absorbs fluid so as to expand and block the hollow anatomical structure. Alternatively, the occluding device can be cured, solidified, or formed in situ. For example, an occluding material is injected into a hollow anatomical structure and cured or solidified in place, the solidified material forming an occluding device.

In a particularly preferred embodiment, a bioabsorbable material is injected into a hollow anatomical structure to occlude the hollow anatomical structure. As the material absorbs fluid and is replaced by fibrous tissue, the hollow anatomical structure is permanently closed using the body's natural healing response. While bioabsorbable materials are particularly preferred, in certain embodiments it can be preferred to employ a biocompatible material that is not bioabsorbable, or to employ a bioerodable material (for example, a material that becomes comminuted upon exposure to physiological conditions).

Occlusion of the Hollow Anatomical Structure

Occlusion of the hollow anatomical structure can be achieved by various mechanisms, and can be permanent or temporary. For example, the occlusion can be achieved by permanent or temporary blockage of the hollow anatomical structure by the occluding device, which acts as a barrier to flow of fluid (e.g., gas, liquid) through the hollow anatomical structure. Alternatively, the occluding device can form a temporary (e.g., biodegradable) or permanent scaffold for growth of tissue, wherein the tissue ultimately forms the occlusion. Similarly, the occluding device can induce formation of an organized thrombus.

In an alternative embodiment, occlusion of the hollow anatomical structure is achieved by using, e.g., tissue adhesives which adhere opposing walls to each other in order to collapse the hollow anatomical structure and eventually result in permanent occlusion of the hollow anatomical structure, e.g., by the formation of scar tissue. Occlusion of the hollow anatomical structure by adhering opposing walls together is preferably achieved by injecting a tissue adhesive into the hollow anatomical structure, then applying compression or a vacuum to collapse the hollow anatomical structure, causing the walls to contact and adhere. Alternatively, compression or vacuum, or another method can be employed to collapse the hollow anatomical structure. After the hollow anatomical structure is collapsed, an adhesive is injected into the collapsed hollow anatomical structure, the adhesive adhering the collapsed walls to each other. Once adhesion is achieved, then the vacuum, compression, or other force collapsing the hollow anatomical structure is removed, and the walls remain adhered to each other. An alternative method for collapsing the hollow anatomical structure utilizes a spreader. The spreader is placed into the hollow anatomical structure to force the sides of the vessel outward to collapse, thereby coapting (i.e., placing in close proximity or contact or cause to adhere by physical proximity or conglutination) the walls of the hollow anatomical structure to improve proximity and reduce interior space in order to improve durability or quality of the occlusion. Application of external linear compression on the outside of the hollow anatomical structure can also be employed to collapse or coapt the walls. In preferred embodiments, compression of the hollow anatomical structure is employed in conjunction with use of an adhesive to achieve occlusion. However, in other embodiments it can be preferred to use compression alone, or adhesive alone.

Occlusion of the hollow anatomical structure can be contiguous or non-contiguous. In contiguous occlusion, all, or substantially all, of the volume to be occluded is filled with an occluding device or material, or sealed with a tissue adhesive. In non-contiguous occlusion, only a portion of the volume to be occluded is filled with an occluding device or material. For example, one end of a hollow anatomical structure can be occluded with an occluding device or material, such as a bioabsorbable material. By sealing one end of the hollow anatomical structure, the volume behind the occluding device or material is effectively blocked to fluid flow. Alternatively, both ends of a hollow anatomical structure can be sealed with an occluding device or material, and the volume between the ends left open. In these embodiments, the occluding device or material is preferably a bioabsorbable material. However, a tissue adhesive can also be employed to occlude one end of a hollow anatomical structure, or both ends of a hollow anatomical structure, leaving the middle open. Over time this open section can be occluded by the body's healing response.

When the hollow anatomical structure possesses a valve, an occluding material or tissue adhesive can be applied on or around valve to close the valve off and prevent flow through it. A second or third occluding device or material can be employed on one or both sides of the valve to contain in place the material or adhesive applied on or around the valve. Alternatively, one or two separate occluding devices can be employed to contain a material in a hollow anatomical structure between the occluding devices. These occluding devices can form temporary occlusions or permanent occlusions. For example, an occluding device can be employed to seal one end (or two occluding devices can be employed to seal two ends) of a hollow anatomical structure such that a temporary vacuum in the hollow anatomical structure can be formed to aid in collapsing or coapting the hollow anatomical structure, or to aid in reducing the volume of the hollow anatomical structure. A tissue sealant can then be injected into the collapsed space to seal the walls together. Once the walls are sealed together, the occluding device can be removed or left in place. Alternatively, a temporary occluding device can block a hollow anatomical structure, and a bioabsorbable material in liquid form can be injected against the temporary occluding device and permitted to cure or solidify in place. Once the bioabsorbable material has cured or solidified, the temporary occluding device can be removed.

As discussed above, bioabsorbable materials are particularly preferred for use in forming occlusions in hollow anatomical structures. The bioabsorbable material provokes a fibrotic response, whereby the bioabsorbable material is replaced as tissue builds up, whereby the tissue forms an occlusion. Preferably, the bioabsorbable material can be inserted into the hollow anatomical structure by injection. The bioabsorbable material can be placed by a single injection into, or surrounding, the hollow anatomical structure to be occluded. Alternatively, multiple injections can be employed, either at the same site, or at a series of different sites, at the same time, or at different times.

Methods employing multiple injections of bioabsorbable materials can offer certain benefits. For example, a small amount of material can be injected, permitted to cure or solidify, then additional material can be added to the same site in one or more additional injections, thereby building up a cured or solidified structure of bioabsorbable material in the hollow anatomical structure. Alternative, a first material can be injected at a site, and then a second, different material can be injected at the same site or a different site. Additional injections of the same material, or one or more different materials, can then be conducted. When the bioabsorbable material cures or solidifies in place, it can be preferred to inject the uncured or fluid bioabsorbable material into the hollow anatomical structure, then inject a cure initiator, catalyst, or accelerator into or adjacent to the material, to facilitate formation of a cured or solidified bioabsorbable material. Alternatively, the cure initiator, catalyst, or accelerator can be injected first, then the prepolymer.

As discussed above, a variety of bioabsorbable materials can be employed. Particularly preferred bioabsorbable materials expand after placement, facilitating effective occlusion of the hollow anatomical structure. For example, a hydrogel can be employed that absorbs water or another fluid from the surrounding environment. Other materials can exhibit swelling or expansion upon exposure to heat (e.g., body temperature), or to physiological conditions (e.g., pH).

In particularly preferred embodiments, an injectable bioabsorbable or biocompatible material is employed that is sufficiently viscous or thick so as not to exhibit an undesired degree of migration from the site at which it is placed. An injectable bioabsorbable or biocompatible material that exhibits adhesive properties is also particularly preferred for migration prevention or inhibition.

Occlusion of the Hollow Anatomical Structure by Fibrotic Tissue Formation

While it is generally preferred to achieve occlusion of the hollow anatomical structure by placing an occluding device or occluding material in the hollow anatomical structure, occlusion can also be achieved by placing an occluding device or material in the perivenous space. In a preferred embodiment, an occluding material is injected into the perivenous space, or in a fascial compartment exterior to a vein. The occluding material can shrink upon curing or solidifying, or release a venoconstrictor and/or sclerosant, thereby occluding the vein. In this embodiment, migration of the occluding material can be avoided, since the material is not subjected to forces from fluid flowing through the hollow anatomical structure. Biocompatibility concerns can also be reduced, since the occluding material is not in contact with circulating blood.

In certain preferred embodiments, blood collects and coagulates in, around, or near the occluding device or occluding material. A thrombus is formed and eventually fibrous tissue grows. In some techniques, a growth factor can be used with the occluding device or occluding material to promote fibrous tissue growth. In some embodiments, a thrombin coating or seeding of the occluding device or occluding material can promote better tissue ingrowth. There are many ways to stimulate tissue ingrowth in a biodegradable polymer. One method is to create a loose polymer scaffold and fill the interstitial space with hydrogel, e.g., fibrin gel. Fibrin gel induces tissue ingrowth. Tissue growth factor, e.g., fibroblast growth factor, can also be incorporated into the occluding device or occluding material with the hydrogel to promote tissue ingrowth. In this approach, the occluding device or occluding material is delivered first, and then fibrinogen, thrombin, and/or growth factor solution is injected into the vein. The solution fills in the interstitial space in the occluding device or occluding material and polymerizes to form hydrogel, which serves as a matrix for rapid tissue ingrowth. An alternative approach to the fibrin gel is to directly mix autogenous blood with thrombin and inject the mixed blood into the vein near the occluding device or occluding material. This creates a blood clot-like structure to fill the space and the clot property can be controlled by thrombin concentration. An occluding device or occluding material comprising thrombin is effective in inducing tissue ingrowth and has advantages over natural clotting. According to another technique, a mix of autologous blood and fibrin is injected just before the occluding device or occluding material is deployed so that it contacts or penetrates the occluding device or occluding material when it is introduced into the hollow anatomical structure.

Additionally, there are other modifications that can be made to the occluding device or occluding material. The surface of the occluding device, as well as the occluding material itself, can be modified, e.g., charge modified, chemically modified, porosified, or roughened to be preferentially fibrinogen-philic or albumin-phobic. Within the first 1-3 seconds after implantation of a hydrophobic device or material in the blood plasma stream, protein begins to adsorb on the surface. Just as immediately, Factor XIIa is activated, starting the clotting cascade. If albumin preferentially lays down on the device or material, it will tend to passivate the surface, rendering it less reactive. Thus, it is advantageous to prevent or limit albumin adsorption and to preferentially adsorb fibrinogen onto the surface of the device or material by adjusting the polymer, or surface of the polymer, charging the surface, or by otherwise increasing its hydrophobicity. In some embodiments, pre-adsorption of fibrinogen onto the device or incorporation of fibrinogen into the material promotes non-passivation. Fibrinogen adsorption causes blood to not see the implant and thus helps to prevent any endothelialization of the clot. In some embodiments, making surface modifications can improve fibrotic occlusion, with or without adding thrombin. By the intrinsic clotting cascade mechanism, thrombin acts on the fibrinogen (a reactive protein monomer circulating in blood plasma, liquid) to become fibrin monomers, which are then cross linked by Factor XIII to become fibrin (a solid). This cross linked fibrin forms an organized thrombus (i.e., a fibrotic occlusion). One example of a material capable of forming an occlusion by this type of mechanism is rough-surfaced DACRON®. DACRON® is a hydrophobic polyester fiber comprising a condensation polymer obtained from ethylene glycol and terephthalic acid, which preferentially adsorbs fibrinogen over albumin, quickly creating fibrin and thus mural (wall) thrombus, and helping to prevent endothelialization. Silicones and polyurethanes do not activate the clotting cascade as aggressively because they both preferentially adsorb albumin over fibrinogen.

Other mechanisms that assist in the formation of fibrotic occlusions include inhibiting the natural fibrinolytic system in the region of the occluding device or occluding material. As mentioned earlier, Factor XIIa starts the clotting cascade, but it also converts plasminogen to plasmin. Plasmin is not desired because it is the enzyme that lyses thrombus. By inhibiting the conversion of plasminogen to plasmin, the natural drive to lyse the desired thrombus in the region of the implant can be prevented. Plasmin is similar to thrombin, except that thrombin only cleaves fibrinogen to create fibrin monomers, which is desired for thrombus formation. In contrast, plasmin cleaves both fibrinogen and fibrin, creating fibrin split products (FSPs) or fibrin degradation products. These are normally removed, but if they are not, they reach high concentrations and become potent inhibitors of clot formation. FSPs inhibit cross linking of the fibrin monomers by preventing them from contacting each other and thereby creating a fibrotic occlusion. Tissue plasminogen activator (tPA) can be used for thrombolysis, as well as other drugs like ReoPro (a GPIIb/IIIa inhibitor that binds to human platelet IIb/IIIa receptors to prevent platelet aggregation). Drugs or surface coatings, such as tissue plasminogen de-activator (tPDA), can be employed to cause platelets to aggregate more aggressively and/or promote aggressive prevention of activation of plasminogin in the region of the occluding device or occluding material.

Kits for Initiating Occlusion of a Hollow Anatomical Structure

The bioabsorbable material and other components can be provided to an administering physician or other health care professional in the form of a kit. The kit is a package which houses a container which contains the bioabsorbable material in uncured or fluid form, or in the form of a two or more component mixture that can be mixed to form a material that shortly thereafter cures or solidifies in place after injection. The kit may optionally also contain one or more other therapeutic agents. The kit can optionally contain one or more diagnostic tools and instructions for use. For example, a kit can contain a bioabsorbable material, as described herein, and directions for placing an occlusion. The kit can contain suitable delivery devices, e.g., syringes, catheters, and the like, along with instructions for placing the occlusion. The kit can optionally contain instructions for storage, reconstitution (if applicable), preparation, and administration of any or all bioabsorbable materials or other materials included in the kit. The kits can include a plurality of containers reflecting the number of occlusions to be situated in a subject.

Prevention of Migration of Occluding Device

To assist the occluding device in remaining in place after insertion, it can be advantageous to employ certain materials or methods to yield a more stable occlusion. For example, the occluding device can include one or more tissue adhesives. Venoconstrictors can be employed to reduce the volume of the hollow anatomical structure, facilitating formation of an effective occlusion. The hollow anatomical structure can be overfilled with an occluding material, making a diameter of the treated segment larger than that of the distal hollow anatomical structures. Multiple injections can be employed. For example, one material can be employed as an occluder for the length of a treated segment, and another material can be used in smaller amounts at one end of a treated segment to prevent migration. As an example, an adhesive, solid plug, venoconstrictor, or heat can be employed to occlude one or more ends of a hollow anatomical structure, and a sclerotherapeutic agent or tissue adhesive can be injected into the length of the hollow anatomical structure between the occluded ends.

In a preferred embodiment, occlusion of the hollow anatomical structure is achieved using a tissue adhesive in conjunction with a short term venoconstrictor administered before, during, or after insertion of the tissue adhesive in the hollow anatomical structure. The venoconstrictor produces apposition of vein walls during the critical curing or solidifying time of the adhesive, then the adhesive takes over to maintain the walls in apposition when the chemical constriction caused by the venoconstrictor wears off. Similarly, an occluding device consisting of a substance that shrinks upon application of heat, e.g., collagen, with a tissue adhesive can be employed. After insertion, the collagen is caused to shrink by application of heat, but the adhesive maintains the constriction of the hollow anatomical structure after shrinkage is completed.

Occlusion of a hollow anatomical structure can also be achieved by an exothermic reaction of bioerodable material. For example, cyanoacrylate based adhesives generate heat when curing is initiated upon contact with moisture in tissue. The heat generated during the process facilitates occlusion of the hollow anatomical structure, e.g., by causing heat induced tissue damage. Other systems can also be employed that generate heat, e.g., a two component system which generates heat when mixed. The system can facilitate occlusion through generation of heat alone, or the system can perform other functions, e.g., tissue adhesion, chemical induced sclerosis, and the like.

In certain embodiments, hollow anatomical structure occlusion is preferably attained by employing a bioabsorbable material wherein the viscosity of the material is adjustable. A low viscosity bioabsorbable material can facilitate delivery, especially to small diameter hollow anatomical structure, while a high viscosity bioabsorbable material can resist migration and effectively block blood flow. The viscosity of the bioabsorbable material can be time dependent (e.g., viscosity increases with passage of time), temperature dependent (e.g., becomes more or less viscous upon application of heat or at body temperature, or curing is thermally initiated), moisture dependent (e.g., moisture acts as a catalyst to a curing reaction), chemical dependent (e.g., a chemical acts as a curing agent), or photochemically dependent (e.g., light, such as ultraviolet light, initiates curing). Examples of Insertion of Bioabsorbable Material Using Catheter Any suitable catheter can be employed for placing the bioabsorbable material in the hollow anatomical structure. Catheters include various designs, including single and multiple lumen designs. In a preferred embodiment, a single lumen tube is employed wherein the bioabsorbable material is injected into the hollow anatomical structure through a distal leg of the catheter. Alternatively, a single lumen catheter incorporating side holes can be employed. In a preferred embodiment, bioabsorbable material is injected into the hollow anatomical structure at a point furthest away from the access site. The catheter is then pulled back while injecting bioactive agent through the catheter (e.g., paint style injection). Pull back injection techniques can be employed with any suitable catheter design, including catheters with a distal leg, or catheters permitting side hole injection.

In certain embodiments, a needle can be employed in placing the occluding material. Any suitable syringe can be employed, which utilizes a needle of suitable length and bore for the hollow anatomical structure to be occluded. Preferably, a needle of a length of about 1 inch or less to about 5 inches or more is employed, more preferably, about 1.5 or 2 inches to about 2.5, 3, 3.5, 4, or 4.5 inches. Preferably, the bore of the needle is from about 0.10" or less to about 0.01" or more. A larger bore can facilitate delivery of viscous occluding materials.

Use of catheters to deliver a polymer to the interior surface of a tissue lumen is disclosed in U.S. Pat. No. 6,699,272 to Slepian, et al. the contents of which are hereby incorporated by reference in their entirety.

Curable or Solidifiable Biodegradable Materials

In a particularly preferred embodiment, occlusion of a hollow anatomical structure is achieved using a biodegradable polymer which can be inserted into the hollow anatomical structure as a liquid via, for example, a syringe and needle, but which solidifies or cures shortly after dosing to form a solid. Such biodegradable polymers are described in U.S. Pat. No. 4,938,763 to Dunn, et al., the contents of which are hereby incorporated by reference in their entirety. Such polymers slowly biodegrade within the body and allow natural tissue to grow and replace the polymer as it disappears. One particularly preferred polymer is poly(DL-lactide-co-glycolide).

In one embodiment, a biodegradable polymer is dissolved in a biocompatible solvent to form a liquid, which can then be inserted into the hollow anatomical structure via a syringe and needle. As the solvent migrates from within the polymer matrix, the polymer cures or solidifies, yielding a solid structure that occludes the hollow anatomical structure. Suitable biodegradable polymers include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyhydroxyalkanoates (PHAs), polyalkylene oxalates, polyalkylene succinates, poly(malic acid), poly(amino acids), polyvinylpyrrolidone, polyethylene glycol, polyhydroxycellulose, chitin, chitosan, and copolymers, terpolymers, or combinations or mixtures of these materials. It is preferred that the biodegradable polymer is nontoxic. However, in certain embodiments it can be desirable for the polymer to exhibit some degree of cytotoxicity, which facilitates the occlusion process. It is preferred that the solvent for the biodegradable polymer be nontoxic, water miscible, and otherwise biocompatible. Cytotoxic solvents can be preferred in certain embodiments for facilitating occlusion. Examples of suitable solvents include N-methyl-2-pyrrolidone, 2-pyrrolidone, ethanol, propylene glycol, acetone, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacycloheptan-2-one.

In an alternative embodiment, a thermosetting functionalized biodegradable or bioabsorbable polymer system is inserted into the hollow anatomical structure, then crosslinked in place. The thermosetting system can comprise a reactive, liquid, oligomeric polymer or polymers which cure or solidify in place, typically with the addition of a curing catalyst. The biodegradable polymers previously described can be employed in thermoplastic systems, after addition of functional groups on the ends of the prepolymer which can be reacted with acryloyl chloride to produce acrylic ester capped prepolymers. Alternatively, the biodegradable polymer can be functionalized with other suitable systems to yield a thermosetting polymer system.

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method for occluding a hollow anatomical structure in a patient, the method comprising:
reducing an interior cross-sectional area of the hollow anatomical structure by applying a vacuum to an interior of the hollow anatomical structure; and
placing an occluding material at an occlusion site, whereby an occlusion is formed in the hollow anatomical structure.

2. The method of claim 1, further comprising a step of:
identifying an occlusion site, wherein the step of identifying is conducted before the step of placing an occluding material at the occlusion site.

3. The method of claim 1, wherein the occluding material comprises a tissue adhesive.

4. The method of claim 3, wherein the tissue adhesive is a cyanoacrylate adhesive.

5. The method of claim 3, wherein the tissue adhesive is selected from the group consisting of collagen, fibrinogen, fibronectin, vitronectin, laminin, thrombin, gelatin, and mixtures thereof.

6. The method of claim 1, wherein the area is reduced by applying a compression to the hollow anatomical structure.

7. The method of claim 1, wherein the hollow anatomical structure is a blood vessel, and wherein the area is reduced by administering a venoconstrictor to the patient.

8. The method of claim 1 wherein the step of reducing an interior cross-sectional area is conducted before the step of placing an occluding material at the site.

9. The method of claim 1 wherein the step of reducing an interior cross-sectional area is conducted after the step of placing an occluding material at the site.

10. The method of claim 1, wherein the occluding site is near at least one valve in a vein.

11. The method of claim 1, wherein the occluding fluid material comprises a hydrogel, wherein the hydrogel expands in situ to occlude the hollow anatomical structure.

12. The method of claim 1, wherein the step of placing an occluding material comprises the steps of:
    placing at least one temporary occluding device in the hollow anatomical structure adjacent to the site;
    placing an occluding fluid material at the site adjacent to the temporary occluding device;
    solidifying or curing the occluding fluid material, whereby an occlusion is formed in the hollow anatomical structure; and
    removing the temporary occluding device.

13. The method of claim 1, wherein the occluding material forms a contiguous occlusion.

14. The method of claim 1, wherein the step of placing an occluding material comprises the steps of:
    placing at least one occluding device in the hollow anatomical structure adjacent to the site, whereby a contiguous occlusion is formed;
    placing an occluding fluid material at the site adjacent to the occluding device; and
    solidifying or curing the occluding fluid material, whereby an occlusion is formed in the hollow anatomical structure.

15. The method of claim 1, wherein the occluding fluid material is placed at at least two separate locations, forming two noncontiguous occlusions.

16. The method of claim 15, wherein a sclerosant is placed between the two noncontiguous occlusions.

17. The method of claim 1, wherein the occlusion site is interior to the hollow anatomical structure.

18. The method of claim 1, wherein the occlusion site is exterior to the hollow anatomical structure.

19. The method of claim 1, wherein the occluding material comprises a collagen plug.

20. The method of claim 1, wherein the occluding material is an alpha-hydroxy acid plug.

21. The method of claim 1, wherein the occluding material comprises a collagen sponge.

22. The method of claim 1, wherein the occluding material is an alpha-hydroxy acid sponge.

23. The method of claim 1, wherein the occluding material includes a therapeutic agent selected from the group consisting of anti-inflammatory agents, anti-infective agents, anesthetics, pro-inflammatory agents, cell proliferative agents, tretinoin, procoagulants, and combinations thereof.

24. The method of claim 1, wherein the occluding material is in a fluid form that cures in situ to form an occlusion in the hollow anatomical structure.

25. The method of claim 1, wherein the occluding material changes viscosity in situ to form an occlusion in the hollow anatomical structure.

26. The method of claim 1, wherein the occluding material is placed in the hollow anatomical structure through a needle.

27. The method of claim 1, wherein the occluding material is placed in the hollow anatomical structure through a catheter.

28. The method of claim 1, wherein the hollow anatomical structure is a vein, further comprising the step of:
    placing a sclerosant in the vein.

29. The method of claim 1, wherein the occluding material comprises a sclerosant.

30. The method of claim 29, wherein the occluding material further comprises dimethyl sulfoxide.

31. The method of claim 1, wherein the occluding material is combined with a sclerosant.

32. The method of claim 29, wherein the occluding material is in a form of a sponge, and wherein the sclerosant is contained on or within the sponge.

33. The method of claim 1, wherein the occlusion is a partial occlusion.

34. The method of claim 1, wherein the occlusion is a complete occlusion.

35. The method of claim 1, wherein the hollow anatomical structure is part of the superficial human venous system of the lower extremities.

36. The method of claim 1, wherein the hollow anatomical structure is a vein selected from the group consisting of the great saphenous vein, the small saphenous vein, a perforating vein which connects superficial veins to deep veins in the leg, and a superficial tributary vein of the leg.

37. The method of claim 1, wherein the hollow anatomical structure is selected from the group consisting of telangiectasia, internal spermatic vein, ovarian vein, gonadal vein, hemorrhoidal vessel, esophageal varices, fallopian tube, vas deferens, arteriovenous malformation, arteriovenous fistula network, aortic aneurysm excluded lumens post abdominal aortic aneurysm graft placement, lumbar artery, and feeding vessel into the aorta.

38. The method of claim 1, wherein the step of identifying an occlusion site in a hollow anatomical structure utilizes an identification method selected from the group consisting of ultrasound, compression, palpation, endoscopy, fluoroscopy, and use of contrast media.

39. A method for occluding a hollow anatomical structure in a patient, the method comprising:
    placing an occluding material at an occlusion site, whereby an occlusion is formed in the hollow anatomical structure;
    wherein the hollow anatomical structure is a vein, and wherein placing an occluding material at the site comprises placing a material in a perivenous space surrounding the vein at the occlusion site, whereby an occlusion is formed in the vein;
    wherein the material is shrinkable, and wherein an occlusion is formed in the vein by shrinking the material.

40. The method of claim 39, wherein the material is collagen, and wherein the step of shrinking comprises heating the collagen.

41. The method of claim 39, further comprising reducing an interior cross-sectional area of the vein.

42. The method of claim 41, wherein the area is reduced by applying a vacuum to an interior of the vein.

43. The method of claim 41, wherein the area is reduced by administering a venoconstrictor to the vein.

44. The method of claim 39, further comprising placing a sclerosant in the vein.

45. The method of claim 39, wherein the vein is part of the superficial human venous system of the lower extremities.

46. A method for occluding a hollow anatomical structure in a patient, the method comprising:
   placing an occluding material at an occlusion site, whereby an occlusion is formed in the hollow anatomical structure;
   wherein the hollow anatomical structure is a vein, and wherein placing an occluding material at the site comprises placing a material in a perivenous space surrounding the vein at the occlusion site, whereby an occlusion is formed in the vein;
   wherein the material is an alpha-hydroxy acid.

47. The method of claim 46, further comprising reducing an interior cross-sectional area of the vein.

48. The method of claim 47, wherein the area is reduced by applying a vacuum to an interior of the vein.

49. The method of claim 47, wherein the area is reduced by administering a venoconstrictor to the vein.

50. The method of claim 47, wherein reducing an interior cross-sectional area is conducted before placing an occluding material at the site.

51. The method of claim 47, wherein reducing an interior cross-sectional area is conducted after placing an occluding material at the site.

52. The method of claim 46, further comprising placing a sclerosant in the vein.

53. The method of claim 46, wherein the vein is part of the superficial human venous system of the lower extremities.

54. A method for occluding a hollow anatomical structure in a patient, the method comprising:
   placing an occluding material at an occlusion site, whereby an occlusion is formed in the hollow anatomical structure;
   wherein the hollow anatomical structure is a vein, and wherein placing an occluding material at the site comprises placing a material in a perivenous space surrounding the vein at the occlusion site, whereby an occlusion is formed in the vein;
   wherein the material is collagen.

55. The method of claim 54, further comprising reducing an interior cross-sectional area of the vein.

56. The method of claim 55, wherein the area is reduced by applying a vacuum to an interior of the vein.

57. The method of claim 55, wherein the area is reduced by administering a venoconstrictor to the vein.

58. The method of claim 55, wherein reducing an interior cross-sectional area is conducted before placing an occluding material at the site.

59. The method of claim 55, wherein reducing an interior cross-sectional area is conducted after placing an occluding material at the site.

60. The method of claim 54, further comprising placing a scierosant in the vein.

61. The method of claim 54, wherein the vein is part of the superficial human venous system of the lower extremities.

* * * * *

UNITED STATES PATENT AND TRADEMARK OFFICE
CERTIFICATE OF CORRECTION

PATENT NO.        : 7,402,320 B2
APPLICATION NO.   : 11/213202
DATED             : July 22, 2008
INVENTOR(S)       : Michael Stephan Mirizzi et al.

It is certified that error appears in the above-identified patent and that said Letters Patent is hereby corrected as shown below:

On page 2, column 2, line 17, under OTHER PUBLICATIONS, delete "cytocompatibiilty"," and insert -- cytocompatibility", --, therefor.

On page 2, column 2, line 22, under OTHER PUBLICATIONS, delete ""Biodegradtion" and insert -- "Biodegradation --, therefor.

At column 4, line 34, delete "the." and insert -- the --, therefor.

At column 5, line 41, delete "structure" and insert -- structure. --, therefor.

At column 6, line 62, delete "unsolidifed" and insert -- unsolidified --, therefor.

At column 8, line 61, delete "needle)," and insert -- needle, --, therefor.

At column 9, line 21, delete "acid)." and insert -- acid. --, therefor.

At column 9, line 26, delete "hydrolysis" and insert -- hydrolysis. --, therefor.

At column 11, line 36, delete "multicomponent" and insert -- multi-component --, therefor.

At column 14, line 45, delete "melenamic" and insert -- mefenamic --, therefor.

At column 14, line 49, delete "betamethesone" and insert -- betamethasone --, therefor.

At column 14, line 58-59, delete "aminoclycosides" and insert -- aminoglycosides --, therefor.

At column 15, line 35, delete "pullulin" and insert -- pullulan --, therefor.

At column 21, line 15, delete "cross linked by" and insert -- cross-linked by --, therefor.

At column 21, line 16, delete "cross linked fibrin" and insert -- cross-linked fibrin --, therefor.

At column 21, line 52, delete "plasminogin" and insert -- plasminogen --, therefor.

UNITED STATES PATENT AND TRADEMARK OFFICE
CERTIFICATE OF CORRECTION

PATENT NO. : 7,402,320 B2
APPLICATION NO. : 11/213202
DATED : July 22, 2008
INVENTOR(S) : Michael Stephan Mirizzi et al.

It is certified that error appears in the above-identified patent and that said Letters Patent is hereby corrected as shown below:

At column 23, line 3-4, delete "Examples of Insertion of Bioabsorbable Material Using Catheter" and insert it as a new heading on Col. 23, Line 4.

At column 28, line 29, in Claim 60, delete "scierosant" and insert -- sclerosant --, therefor.

Signed and Sealed this

Third Day of March, 2009

JOHN DOLL
*Acting Director of the United States Patent and Trademark Office*